United States Patent [19]

Savage

[11] 4,283,204
[45] Aug. 11, 1981

[54] PROCESS FOR THE SEPARATION OF CONTAMINANTS FROM FEED STREAMS USING MAGNETIC BEDS

[75] Inventor: David W. Savage, Summit, N.J.
[73] Assignee: Exxon Research & Engineering Co., Florham Park, N.J.
[21] Appl. No.: 182,937
[22] Filed: Sep. 2, 1980

Related U.S. Application Data

[63] Continuation-in-part of Ser. No. 73,481, Sep. 7, 1979, abandoned.
[51] Int. Cl.³ .................................... B01D 50/00
[52] U.S. Cl. .................................... 55/3; 55/34; 55/62; 55/73; 55/79; 55/99; 55/100; 55/75; 55/61; 34/1; 34/10; 55/208
[58] Field of Search .................. 34/1, 10; 55/3, 33, 55/34, 74, 75, 77, 79, 59, 60, 99, 100, 390, 208

[56] References Cited

U.S. PATENT DOCUMENTS

| | | | |
|---|---|---|---|
| 2,549,104 | 4/1951 | Lechthaler | 55/34 |
| 2,583,239 | 1/1952 | Teter | 55/79 |
| 2,642,955 | 6/1953 | Huntington | 55/34 |
| 2,738,857 | 3/1956 | Drew | 55/34 |
| 3,007,545 | 11/1961 | Kimberlin et al. | 55/77 |
| 3,067,131 | 12/1962 | Bergstrom | 55/3 |
| 3,078,640 | 2/1963 | Milton | 55/73 |
| 3,093,465 | 6/1963 | Latta | 55/60 |
| 3,177,631 | 4/1965 | Tamura | 55/79 |
| 3,494,046 | 2/1970 | Harkreader . | |
| 3,594,983 | 7/1971 | Yearout | 55/53 |
| 3,960,529 | 6/1976 | Juntgen et al. | 55/390 |
| 4,070,164 | 1/1978 | Miwa et al. . | |
| 4,104,806 | 8/1978 | Reusch . | |
| 4,115,927 | 9/1978 | Rosensweig | 55/100 |
| 4,132,005 | 1/1979 | Coulaglou | 34/1 |
| 4,157,245 | 6/1979 | Mitchell et al. | 34/10 |
| 4,194,864 | 4/1979 | Eakman et al. . | |

FOREIGN PATENT DOCUMENTS

66178  5/1967  Australia .................................... 55/61

OTHER PUBLICATIONS

Ermenc–Designing a Fluidized Bed Adsorber Chem. Engineering, May 29, 1961, pp. 87–94.
Somov et al.–Heat Transfer, Soviet Research, vol. 8, No. 6, Nov.–Dec. 1976, pp. 81–90.
Greirmer et al.–Separation N–Paraffins With Isosiv–Hydrocarbon Processing 44, pp. 147–150 (1965).
Schumacher et al.–Separation of Hydrocarbons in Fired Beds of Mol. Sieves I & EC Process Design Development 6, pp. 321–323, 1967.
Ruthven et al.–The Sorption and Diffusion of N-Butane in Linde 5A Molecular Sieve Chem. Engr. Science 26, pp. 1145–1154, 1967.
Etherington et al.–Fluid Char. Adsorption Process Chem. Engr. Progress, pp. 274–280, Jul. 1956.
Barry–Fixed Bed Adsorption Chem. Engr., Feb. 1960, pp. 105–120.
Separation of N-Hexane from Solution in Benzene by Adsorption on Molecular Sieve 5A–Kehat et al.–I & EC Process Design and Development 4, pp. 217–220 (1965).
Drying of Air by Fixed Bed Adsorption With Mol Sieves–Nutter et al., Aiche Journal, pp. 202–206, 3–63.

*Primary Examiner*—Bernard Nozick
*Attorney, Agent, or Firm*—Albert P. Halluin

[57] ABSTRACT

The present invention relates to a process for the separation of components or mixtures from feedstreams using magnetically stabilized beds. More particularly, the invention relates to the removal of contaminants from fluid streams in a continuous process by use of solid absorbents which also include a magnetizable component capable of adsorbing the contaminants from the fluid streams wherein the adsorption and desorption are carried out at substantially the same pressure. The adsorbent particles and magnetizable component which flow or move through the vessel are stabilized against fluid by-passing and solids back-mixing and recirculation generally associated with fluidized beds (except for the flow or movement of the solids through the contacting vessels) during adsorption and desorption by the use of an applied magnetic field. The use of the applied magnetic field enables one to use small size adsorbent particles without encountering high pressure drops as with fixed bed processes. The small adsorbent particles give faster transfer of the contaminants than with larger particles which allows for closer approach to equilibrium, the use of smaller beds than by use of fixed beds and the possibility of using one bed rather than a multiplicity of beds as with fixed bed processes.

16 Claims, 2 Drawing Figures

PROCESS FOR THE SEPARATION OF CONTAMINANTS FROM FEED STREAMS USING MAGNETIC BEDS

CROSS-REFERENCE TO RELATED APPLICATIONS

This application is a continuation-in-part of U.S. Ser. No. 73,481, filed Sept. 7, 1979, now abandoned.

FIELD OF THE INVENTION

The present invention relates to a process for the separation of components or mixtures from feed streams using magnetically stabilized beds. More particularly, the invention relates to the removal of contaminants from fluid streams in a continuous process by use of solid adsorbents capable of adsorbing the contaminant(s) from the fluid streams. The adsorbents include a magnetizable component. The adsorbent particles and magnetizable component which flow or move through the vessel are stabilized by the use of an applied magnetic field against gas by-passing and solids back-mixing and recirculation generally associated with fluidized beds (except for the flow or movement of the solids through the contacting vessels) during adsorption and desorption. The use of the applied magnetic field enables one to use small size adsorbent particles without encountering high pressure drops as with fixed bed processes. The small adsorbent particles give faster transfer of the contaminants than with large particles which allows for a closer approach to equilibrium, the use of smaller beds than would be needed in a fixed bed process and the possibility of using one adsorption bed rather than a multiplicity of beds as with fixed bed processes. The invention allows many separation stages to be obtained in a single vessel without incurring high gas-side pressure drop.

DESCRIPTION OF THE PRIOR ART

In conventional separation processes, vapors of the gases to be treated are contacted with adsorbents in fixed beds, a plurality of beds being used so that one or more beds will be undergoing a regeneration step while one or more other beds are being used in the adsorption step of the cycle. It is readily evident that cyclic fixed bed operations have a number of inefficient aspects, including the need for extensive valving and manifolding, as well as pressure swing-product loss, considerable waste of heat in heating up and later cooling down the various flow lines, vessel walls and internal components of the vessel. Although in theory only two vessels need be used for a cyclic operation, one for adsorption and one for regeneration, in actual practice use of more than two vessels is advantageous to reduce the size of the vessels, to reduce stripping gases (product gas loss) and to minimize adsorbent inventory. However, as the number of vessels increases, the time available for regeneration becomes critical, so that there must be provision made for sufficient time intervals to go through all of the regeneration steps, including switching of valves, depressuring, heating, holding at high temperature, cooling and repressuring. See H. M. Barry, Chemical Engineering, pages 105-120, Feb. 8, 1960; E. Kehat et al, *I & EC Process Design and Development*, 4: 217-220 (1965); J. I. Nutter et al, *A.I.CH.E. Journal*, Pages 202-206, March, 1963; G. J. Griesmer et al, *Hydrocarbon Processing*, 44: 147-150 (1965); W. J. Schumacher et al, *I & EC Process Design and Development*, 6: 321-327 (1967); D. M. Ruthven et al, *Chemical Engineering Sciences*, 26: 1145-1154 (1971).

Because of the large plant investment required in fixed bed adsorbent processes, as well as high operating costs, the desirability of employing a continuous countercurrent adsorption process for separating components in feedstreams has long been recognized. The fluidized solids technique is an attractive approach to such a continuous process, because it eliminates the need for valving, manifolding and other facilities required for a fixed bed cyclic operation. A number of patents and publications have disclosed the concept of separating hydrocarbon mixtures by fluidized or simulated fluidized beds. Fluidized bed drying has also been described in the patent literature. For example, see U.S. Pat. Nos. 3,494,046 and 3,104,806 which are concerned with processes for drying particulate matter. However the advantages inherent in the use of fluidized beds for such operations as catalytic cracking and hydroforming of hydrocarbons, namely, complete mixing of solids so as to insure isothermal conditions and maximum heat transfer is a disadvantage in an adsorption process wherein back mixing of solids is not desirable. For this reason, when the use of fluidized solids for adsorption processes has been undertaken, it has required a plurality of vertically spaced shallow fluidized beds providing stagewise contacting of gas and adsorbent. See, for example, L. B. Etherington et al, *Chemical Engineering Progress*, Pages 274-280, July, 1956; and E. D. Ermenc, *Chemical Engineering*, Pages 87-94, May, 1961.

In the present invention, the adsorption and desorption of the contaminant(s) in a feed stream takes place in a fluidized (i.e., expanded and levitated) bed accomplished without the need for a plurality of vertically spaced shallow beds by employing an applied magnetic field to stabilize or structure the fluidized bed. The result is that true countercurrent staged flow of solids with respect to the flow of the fluids, e.g., fluids containing product and contaminants, that fluidize the bed can be obtained with greatly reduced overall investment and operating cost, as compared with what was heretofore possible. The process of the present invention preferably takes advantage of the use of a magnetically stabilized fluidized bed, such as disclosed in U.S. Pat. No. 4,115,927 to R. E. Rosensweig, with particular reference to column 21, lines 16-28, the disclosure of which is incorporated herein by reference.

SUMMARY OF THE INVENTION

The present invention is directed to a process for the separation of contaminant components from a feedstream containing the same, within an external force field, said process comprising the steps of:

(a) adsorbing a portion of the contaminant from said feedstream by countercurrently contacting said feedstream with a bed comprising adsorbent particles capable of adsorbing said contaminant components from said feedstream;

(b) desorbing at least a portion of said contaminant from said adsorbent particles to regenerate at least a portion of said adsorbent particles;

(c) providing a magnetizable component with said adsorbent particles and applying a magnetic field to said magnetizable component and adsorbent particles along the direction of said external force field and at a strength sufficient to prevent and/or suppress gross solids circulation and back mixing;

(d) fluidizing, expanding or levitating said adsorbent particles and magnetizable component by countercurrently contacting said adsorbent particles and magnetizable component with said feedstream; and (e) carrying out said adsorption and desorption steps at substantially the same pressure.

An essential feature of the present invention involves carrying out both the adsorption and desorption steps at essentially the same pressure, i.e., the pressure differential will vary by only about 70 psi or less. Preferably, in some low pressure processes, the pressure differential will be less than about 25 percent from the adsorber pressure but never more than about 70 psi from the adsorber pressure.

Thus, in its broadest sense, the present invention can be defined as a process for separating contaminant components from a feed stream which comprises feeding the feed stream to a bed of adsorbent particles which are admixed or composited with magnetizable particles by countercurrent contacting these particles under fluidization conditions (or where the bed is expanded or levitated by the feed stream) wherein said bed is stabilized by the application of a magnetic field, and recovering the feed stream depleted of said contaminants.

The term "contaminant" as used herein is to be taken in the broadest sense as being substances, molecules or compounds which make "impure" the final product one desires to obtain. Obviously, the contaminant removed from a feedstream in the process of the present invention may itself be valuable. Thus, the term "contaminant" merely refers to the substances, molecules or compounds one wishes to remove from a feedstream, irrespective of the value or lack thereof for the "contaminants".

Examples of some contaminants which may be removed from the feedstreams utilizing the process of the present invention include the acid gases and polar or nonpolar-type compounds.

Typical polar-type compounds (some of which are also acidic) include: $CO$, $COS$, $NH_3$, $H_2S$, $SO_2$, $H_2O$, $HCN$, $RSH$ (wherein R is an organic radical, e.g., mercaptans), $RS$ (wherein R is an organic radical, e.g., $C_4H_4S$), etc. Typical non-polar acid gases include $CO_2$ and $CS_2$.

Typical non-polar compounds include hydrocarbons, e.g., methane, ethane, propane, butane, substituted hydrocarbons, etc.

The process of the invention is preferably carried out by fluidizing, expanding or levitating the adsorbent particles and magnetizable components under countercurrent substantially plug flow conditions by subjecting the adsorbent particles and magnetizable component to a magnetic field, preferably a uniform applied magnetic field having a substantial component along the direction of the external force field (e.g., gravity) such that the magnetizable component has a component of magnetization along the direction of the external force field and wherein a portion of the bed of particles is fluidized by a flow of fluid opposing said external force field at a superficial fluid velocity ranging between:

(a) a lower limit given by the normal minimum fluidization-superficial fluid velocity required to fluidize said bed in the absence of said applied magnetic field, and, (b) an upper limit given by the superficial fluid velocity required to cause time-varying fluctuations of pressure difference through the stably fluidized bed portion during continuous fluidization in the presence of said applied magnetic field.

Preferably, the strength of the magnetic field and its deviation from a vertical orientation are maintained so as to prevent and/or suppress the formation of bubbles in the fluidized or expanded or levitated medium at a given fluid flow rate and with a selected fluidization particles makeup.

The magnetically stabilized fluidized adsorbent-desorbent beds have the appearance of expanded backed beds with substantially no gross solids circulation or recirculation (except for the plug flow movement of the solids through the vessels) and very little or no fluid by-passing. The application of the magnetic field enables one to employ superficial fluid flow rates 2, 5, 10 or 20 or more times the superficial fluid flow rate of the fluidized bed at incipient fluidization in the absence of the applied magnetic fluid, concomitant with the absence of bubbles. In other words, as the superficial fluid velocity is increased, the pressure drop through the bed is similar to that which would be expected from a normal fluidized bed without the application of a magnetic field; it increases to the bed weight support value at the minimum fluidization velocity, and then remains relatively constant as the fluid velocity is increased. This stably fluidized bed condition persists even as the solids are continuously moved in a descending, substantially plug flow manner through the contacting vessels.

DESCRIPTION OF THE PREFERRED EMBODIMENTS

Figure 1:
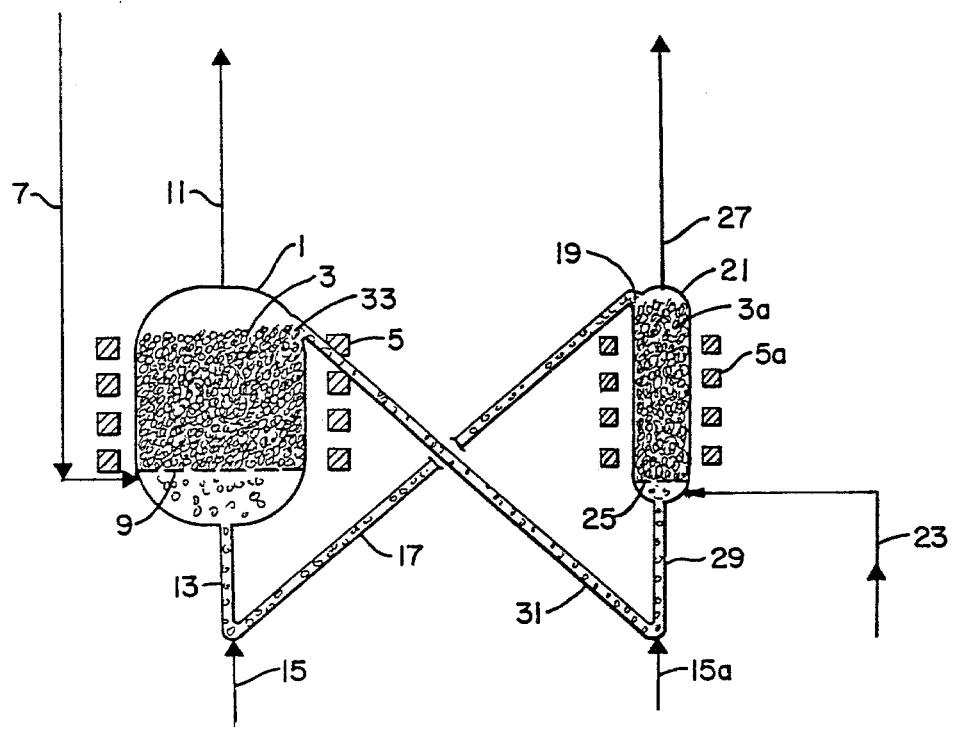
FIG. 1 represents a vertical cross-sectional view of the magnetically stabilized adsorber and desorber (regenerator) wherein the adsorber and desorber are positioned side-by-side.

As indicated previously, the present invention relates to a process for preferentially adsorbing contaminants, e.g. polar or non-polar compounds from a feedstream containing at least one other component which comprises contacting said feedstream under adsorption conditions for said contaminants with a bed containing adsorbent particles and desorbing said adsorbed contaminants from said adsorbent particles whereby a stream enriched in said preferentially absorbed contaminants is obtained, said process being carried out in the presence of a magnetizable component and an applied magnetic field to stabilize or structure the bed containing the adsorbent particles and magnetizable component. By the present process, the separation can be staged.

The adsorbent particles may be used as admixtures or as composites with a ferromagnetic or ferrimagnetic component or substance. All ferromagnetic and ferrimagnetic substances, including, but not limited to, magnetic $Fe_3O_4$, $\gamma$-iron oxide ($Fe_2O_4$), ferrites of the form $MO \cdot Fe_2O_3$, wherein M is a metal or mixture of metals such as Zn, Mn, Cu, etc.; ferromagnetic elements including iron, nickel, cobalt and gadolinium, alloys of ferromagnetic elements, etc., may be used as the magnetizable and fluidizable particulate solids which are used in admixture or composited with the adsorbent particles. Alternatively the adsorbent may itself contain a ferromagnetic or ferrimagnetic substance in its makeup.

In this case, the adsorbent is already magnetic; no additional magnetic material need be admixed or composited with the adsorbent.

The adsorbent particles are generally chosen to suit the particular feed to be treated and the contaminent substance(s) that is to be removed from the feedstream. Inorganic, organic or high molecular weight inorganic or organic adsorbents may be used.

Examples of adsorbents suited for the separation process of the present invention include activated carbons, treated activated carbons, molecular-sieving carbon; nonstoichiometric carbon-sulfur compounds, (e.g., $C_xS$ compounds such as disclosed in U.S. Pat. No. 4,201,665, incorporated herein by reference); selected artificially synthesized zeolites, such as those having some particular ratio of principal components identified as: "Type A"; "Type L"; "Type X"; "Type Y"; "Type ZSM"; mordenite; faujasite; erionite; and the like; those zeolites which have particular silica-alumina ratio and those in which the original sodium cations are exchanged to other cations; selected silica-gels, such as those having some particular relative components of silica, alumina and ferric oxides, those which have particular steric properties as the average pore diameter, specific surface area, pore volume and others; selected activated aluminas such as those having particular components of aluminum oxide and water, those hydrated forms, some particular crystal forms, those which have a particular structure; activated clay or selected acid clays such a montmorillonite in which case the base is exchanged holloysite or attapulgite; aluminas; layered clays.

The aforesaid adsorbents comprising carbon, silica, alumina, metal oxides, iron, magnesium, hydrated oxides and/or other elements are characterized as:

(1) having several different structures, or (2) having different components, and (3) such that some composing elements are substituted by others, followed by further chemical or physical treatment.

Most of the aforesaid adsorbents are readily available in the commercial market. Also the adsorbents similar to those which are commercially available can be generally synthesized without very elaborate technique and many adsorbents can be prepared by chemically or physically treating commercially available adsorbents. A further description of the zeolites mentioned above, and their methods of preparation are given, for example, in U.S. Pat. Nos. 2,882,243; 2,882,244; 3,130,007; 3,410,808; 3,733,390; 3,827,968 and patents mentioned therein, all incorporated herein by reference.

Other adsorbents suitable in the practice of the invention include cation-exchange resins with exchange groups of benzene sulfonic acid, carboxylic acid, phosphoric acid; strongly or weakly basic anion-exchange resins; high molecular weight particles of styrene-divinylbenzene copolymer, or its halomethylated, or cyanoethylated polymers; acrylonitrile copolymers; high molecular weight compounds having several functional groups such as cyano, cyanomethyl, chloromethyl, thioether, sulfone, isocyanate, thiocyante, thiourea, allyl, acetyl-acetone, aldehyde, ketone, aliphatic, anhydride, ester, halogen, nitro and others.

The most suitable adsorbents for achieving high adsorption-desorption rates are activated carbons, molecular-sieving carbon, synthetic zeolites and high molecular weight organic materials. These adsorbents generally show a high exchange rate of adsorbing components, due to their chemical affinity for various contaminant substances such as acid gases, and polar and non-polar-type molecules in the case of high molecular weight materials, and because of the macropores in case of activated carbons, molecular sieving carbon and synthetic zeolites which comprise minute crystals smaller than a few microns, and clay or other binding material.

Typical examples of suitable adsorbents are synthetic zeolite "Type A" for the separation of various polar molecules from gaseous feeds. Type A zeolite has a typical oxide formula $Na_2O.Al_2O_3.2SiO_2.4\frac{1}{2}H_2O$, a typical unit-cell formula $Na_{12}[(AlO_2)_{12}(SiO_2)_{12}].27.H_2O$, a density of 1.99 g/cc, a unit cell constant of 12.32–24.64 Angstroms, a void volume of 0.47 cc/cc, a free aperture of 2.2 Å($\beta$)-4.2 Å($\alpha$), and a kinetic diameter of 3.6–3.9Å.

Synthetic zeolites include a useful class of inorganic adsorbents because the adsorption power of the molecules selected from adsorption on zeolites can easily be altered by exchanging sodium ions which usually come from the original production steps into some other cations to change their crystal structure or electron configurations to the desired forms. Usually Group I metal ions such as lithium, potassium, rubidium, cesium, silver, copper; Group II metal ions such as beryllium, magnesium, calcium, strontium, barium, zinc, cadmium, mercury, titanium, vanadium, chromium, nickel, cobalt, iron, manganese; rare earth metals; uranium; and lead cations or their mixtures are used to replace sodium ions originally contained in the zeolites. The more effective sets of cations are: potassium and lithium; potassium and calcium; potassium and cadmium; potassium and iron; potassium and nickel; potassium and cobalt; potassium and barium; potassium and magnesium; calcium and magnesium; calcium and manganese; lithium and manganese; barium and sodium; barium and lead; iron and uranium; and others. Given a particular feed stream, the most suitable set of cations, their relative compositions, or most effective activation treatments can be easily selected through various experiments, since cation-exchange procedure is readily repeated many times. Generally, Type A synthetic zeolites are exchanged with calcium or magnesium or their mixtures for separating the polar or non-polar molecules from the feed stream.

The adsorbent, i.e., the synthetic zeolite, will typically contain 75-98% of the zeolite component and 2-25% of a matrix, (e.g., binder), component. The zeolites will usually be exchanged with sufficient cations to reduce the sodium level of the zeolite to less than 5 wt. %, preferably less than 1 wt. %. Reference in this regard is made to the following U.S. Pat. Nos. 3,140,249; 3,140,251; 3,140,252 and 3,140,253, which are incorporated herein by reference.

When the magnetizable component is admixed with nonmagnetic adsorbent particles, it is preferred that the volume fraction of the magnetizable component exceed 25 volume percent, more preferably it should exceed 50 volume percent, and preferably more than 60 volume percent, to obtain the greatest bed stability at the lowest applied magnetic field strength.

In case of a composite of the magnetizable component and the adsorbent, the ferromagnetic and/or ferrimagnetic material will comprise 1 to 25, preferably 5 to 15 volume percent based on the total volume of the composite adsorbent. In any event, the composite should have a magnetization of at least 50 gauss, preferably greater than 250 gauss.

One example of preparing the composites of the magnetizable component and the adsorbent is described as follows: the magnetic component such as 400 Series stainless steel, particles and the adsorbent, e.g., the zeolite sieve, are admixed with a base (matrix or binder) for the adsorbent and a relatively homogeneous gel is formed. The adsorbent base may be comprised of, for example, silica, alumina or silica-alumina. The gel may then be dried, calcined and/or sized. Suitable techniques for sizing and shaping the composite adsorbent are extrusion, pilling, beading, spray drying, etc. The magnetizable component may also be composited with the adsorbent by impregnation, cogelling, coprecipitation, etc.

The bed particles (composites or admixtures) will typically have an average mean particle diameter ranging from about 50 to about 1500 microns, preferably from about 100 to about 1000 microns, and more preferably from about 175 to about 850 microns. The particles may be of any shape, e.g., spherical, irregular shaped or elongated.

The application of a magnetic field to the fluidized, expanded or levitated particles containing the magnetizable particles in the adsorption or desorption zones in accordance with the invention is not limited to any specific method of producing the magnetic field. Conventional permanent magnets and/or electromagnets can be employed to provide the magnetic field used in the practice of the present invention. The positioning of the magnets will, of course, vary with the solids used, degree of fluidization required and the effects desired. In the preferred embodiment of the present invention, a toroidally shaped electromagnet is employed to surround at least a portion of the fluidized bed as this provides the most uniform magnetic field and consequently the best stability throughout the bed. The electromagnets may be energized by alternating or direct current, although direct current energized magnetic fields are preferred due to lower costs of operation. Such electromagnets when powered by direct current with the use of a rheostat are particularly desirable for applying a magnetic field to the bed particles and to provide an excellent method of stabilizing the fluidization of the bed particles in response to the flow of the fluidizing medium.

The invention is not limited by the shape or positioning of the magnet employed to produce the magnetic field. The magnet can be of any size, strength or shape and can be placed above or below the bed to achieve special effects. The magnets employed can be placed within or without the vessel and may even be employed as an integral portion of the vessel structure itself. The process is not limited to any particular vessel material and it can be readily adapted for use in contacting vessels currently employed by industry.

The amount of magnetic field to be applied to the fluidized solids in the contacting zones (adsorption and desorption zones) will, of course, depend on the desired magnetization for the magnetizable particles and the amount of stabilization desired. Particles having relatively week magnetic properties, e.g., cobalt, nickel, etc., will require the application of a stronger magnetic field than particulate solids having strong ferromagnetic properties, e.g., iron, to achieve similar stabilization effects. The size and shape of the solids will also obviously have an effect on the strength of the magnetic field to be employed. However, since the strength of the field produced by an electromagnet can be adjusted by adjusting the field strength of the electromagnet, an operator can readily adjust the field strength employed to achieve the desired degree of stabilization for the particular system employed. Specific methods of applying the magnetic field are also described in U.S. Pat. Nos. 3,440,731; 3,439,899; 4,115,927 and 4,143,469; British Pat. No. 1,148,513 and in the published literature, e.g., M. V. Filippov, Applied Magnetohydrodynamics *Trudy Instituta Fizika Akad.Nauk.*, Latviiskoi SSR 12:215–236 (1960); Ivanov et al, *Kinet. Kavel,* 11 (5):1214–1219 (1970); Ivanov et al, *Zhurnal Prikladnoi Khimii,* 45:248–252 (1972); and R. E. Rosenweig, *Science,* 204:57–60 (1979), which are incorporated herein by reference. The most preferred applied magnetic field will be a uniform magnetic field such as described in U.S. Pat. No. 4,115,927. Typically, the empty vessel applied magnetic field, as taught in U.S. Pat. No. 4,115,927, will range from about 50 to about 1500 oersteds, preferably from about 100 to about 600 oersteds and more preferably from about 125 to about 400 oersteds.

The process operating conditions to be employed in the practice of the present invention may vary widely and will include those treating conditions typically employed in the adsorption-desorption separation processes known in the art. As well known, these conditions will generally vary depending on the feedstream being treated, the adsorbent being used, etc. An essential feature of the invention, however, is to carry out the adsorption and desorption at essentially the same pressure, i.e., the pressure differential between the adsorption and desorption zones will vary by no more than about 25 percent, preferable no more than 10–20 percent. As an additional constraint, the pressure differential in magnitude will not exceed about 70 psi. The zones will only vary from about 1 to about 70 psi and preferably the pressure differential will only vary between 10 and 50 psi. Thus, the regeneration (desorption) is done thermally at the same or essentially the same total pressure as in the adsorption zone. The temperatures used in the adsorption zone will be those at which the contaminant(s) to be adsorbed are preferentially adsorbed with the particular adsorbent being used. These temperatures may range from about −200° C. to about 350° C., preferably from about 0° C. to about 300° C., especially preferably from about 10° to about 200° C., and more preferably from about 15° C. to about 150° C. The temperatures during desorption will be at least about 100° C. greater than those at adsorption, preferably 200° C. and more preferably 300° C. greater than the temperatures used during adsorption. The pressures used during the adsorption and desorption steps may range from about 0.1 to about 2000 psi, preferably from about 1 to about 750 psi, and more preferably from about 1 to about 650 psi. The feed stream to be treated in accordance with the process of the invention may be either in a gaseous or liquid state. The superficial fluid velocity of the fluidizing fluid in the case of gas may range from about 0.01 to about 3 m/sec, more preferably from about 0.08 m/sec to about 1.5 m/sec. The superficial fluid velocity of the fluidizing fluid in the case of a liquid may range from about 0.001 cm/sec to about 0.3 cm/sec, more preferably from about 0.008 cm/sec to about 0.15 cm/sec. The bed particles preferably move countercurrently in a substantially plug-flow manner against the ascending feed or stripping gas by the action of gravity or pressure in the contacting vessel(s). The solids movement rate may vary depending on the level of contaminants in the feed, the size of the vessel(s), the feed gas velocity, etc.

The adsorption can take place in any suitable vessel as earlier mentioned. The vessel may be equipped with internal supports, trays, etc. In the lower portion of the adsorption vessel there will be disposed a suitable grid means for distributing the incoming feed. The bottom or lower portion of the adsorption vessel will have means for removing spent solids from the adsorption vessel. This opening may be at the side of the vessel or at its bottom. A pipe grid may be utilized for feeding the gaseous feed, i.e., perforated pipes. By use of a pipe grid the spent solids may flow past the grid by gravity to the regenerator or desorber.

The feed mixture applicable to the process of the present invention may come from a variety of sources, for example, the process of the invention is applicable to the following separation processes: Drying of natural gases prior to liquefaction for LNG; drying of natural gases prior to cryogenic fractionation into high BTU pipeline gas, ethane, etc.; drying steam cracker off-gas prior to cryogenic distillation in ethylene plants; drying catalytic cracking off-gas prior to cryogenic distillations; drying of air prior to liquefaction and distillation to make oxygen and nitrogen; drying of air for various applications such as instrument control systems; drying of recycle hydrogen gas for catalytic reforming for making gasoline and other related drying and separation processes; removal of polar compounds, such as $H_2O$, $H_2S$, $SO_2$, $NH_3$, COS, RSH, etc. from non-polar gases such as natural gas, hydrocarbon gases, e.g., from refineries, hydrogen and mixtures thereof; removal of $CO_2$ or $H_2O$ from non-polar gases; removal of $CO_2$ from cryogenic plant feed gases; removal of sulfur compounds from natural gas; hydrogen purification processes, e.g., (1) from demethanizer off-gas containing hydrogen, $CH_4$, CO, $C_2H_4$, $C_2H_2$, $CO_2$ and $N_2$;

(2) from steam reformer hydrogen containing $CO_2$, $H_2O$, $CH_4$, CO and nitrogen;

(3) from off gas from a catalytic reformer containing hydrogen, $CH_4$, $C_2H_6$, $C_3H_8$, $C_4H_{10}$, and trace amounts of $C_5^+$ hydrocarbons;

(4) from refinery and chemical plant fuel gas streams containing hydrogen, $CH_4$, $C_2H_6$, $C_3H_8$, $C_4H_{10}$, $C_2H_4$, $C_3H_6$, $C_4H_8$, along with trace amounts of $C_5^+$ hydrocarbons, $H_2S$, $CO_2$, $N_2$ and $H_2O$.

(5) from hydrofiners containing hydrogen, $CH_4$, $C_2H_6$, $C_3H_8$, $C_4H_{10}$, $C_2H_4$, $C_3H_6$, $C_4H_8$, along with trace amounts of $C_5^+$ hydrocarbons, $H_2S$, $CO_2$, CO, $N_2$, $NH_3$ and $H_2O$;

(6) from electrolytic off-gas containing $N_2$, $CO_2$ and $H_2O$;

(7) from dissociated $NH_3$ from $N_2$ and $NH_3$; and (8) from $NH_3$ reactive loop purge containing $CH_4$, A, $N_2$, and $NH_3$; methanol reactor loop purge containing CO, $CO_2$, $CH_4$, and $N_2$; removal of organic solvents from air; solvents recovery with activated carbon; adsorption of hydrocarbons from gas streams, e.g., propane and higher hydrocarbons from natural gas; ethane from methane/ethane mixtures; and Krypton 80 removal from air; and (9) methane from air.

The following Table illustrates examples of processes whereby minor amounts of polar molecules and $CO_2$, $CS_2$ and the like may be removed from gaseous streams utilizing the process of the present invention.

TABLE

| Application | Separation Processes To Be Used With Process of the Present Invention | |
|---|---|---|
| | Typical Gas Composition | Components to be Removed |
| • Inert gas purification (1–5 psig) | $N_2$-89%, $CO_2$-11%, $H_2O$-trace | $CO_2$ and $H_2O$ |
| • Ethylene purification (i.e., production of polyethylene plastics) (~300 psig) | Primarily ethylene with traces of $CO_2$ and $H_2O$ | $CO_2$ and $H_2O$ |
| • Cryogenic plant feed gas (~75 psig) | $N_2$, $O_2$, Ar, $CO_2$, $H_2O$, trace hydrocarbons, $NO_x$, etc. | |
| + air feed to $O_2$ plant | | $CO_2$ and $H_2O$ |
| + LNG plant feed | | $CO_2$ and $H_2O$ |
| + refinery light ends | | $CO_2$ and $H_2O$ |
| • Natural gas treatment (1000–1600 psig) | $C_1$–$C_8$ hydrocarbons, small amounts of $N_2$, $H_2S$, RSH, $CO_2$ | $H_2S$, RSH and $CO_2$ |
| • Nitric acid plant tail gas (~1 psig) | $N_2$-95–98%, $O_2$-0–3%, Ar-1.5–2%, $H_2O$-saturated, $NO_x$-150–3000 ppm | $NO_x$ |
| • Flue gas desulfurization (~1 psig) | $N_2$-75–76%, $CO_2$-13–15%, $H_2O$-7–10%, $O_2$-1–3%, $SO_2$-0.25%, $SO_3$-0.005% | $SO_2$ and $SO_3$ |

The adsorbed contaminant molecules are desorbed, as mentioned above by the thermal swing process, i.e., the process which involves heating the spent particles to a temperature where the adsorbent's adsorptive capacity for the contaminant compounds or molecules is reduced to a low level. The removal of the contaminant compounds or molecules trapped between the sorbent particles is enhanced by a suitable purge gas stream, e.g., steam, ammonia, hydrogen or low molecular weight hydrocarbon gases or product gas from the absorber, etc.

A specific generalized example of the process of the present invention comprises contacting a bed of particles of a Type 4A zeolite molecular sieve containing a ferromagnetic component countercurrently with a feed of vapors, e.g., a natural gas and water vapors in the magnetically stabilized adsorption zone. The solids leave the adsorption zone with the water loaded virtually at equilibrium with the feed vapors. The nature of the molecular sieve structure preferentially adsorbs the polar molecules (e.g., water) from the natural gas components. By use of the magnetically stabilized bed, it is possible to use smaller particles than in fixed bed processes and by use of these small particles, reduced diffusion resistance can be realized. Also, the size of the adsorption bed is relatively small compared to a fixed bed of conventional sized sieve particles. The sieve particles flow from the adsorption zone to the magnetically stabilized desorption zone where they move downward countercurrent to the ascending hot purge gas stream. The hot gases heat the spent particles to a temperature where the sieve's adsorptive capacity for the water is reduced to a low level and water is consequently desorbed from the adsorbent. As in the adsorption step, the small particle size reduces diffusion resistance and results in a very close approach to equilibrium between vapors and solids at any given point. As mentioned before, pressures are nearly the same in all the zones, whereas the temperature in the desorption zone is substantially greater than that in the adsorption zone.

Referring now to the drawings, FIG. 1 is shown for explanation of the principles of separation in the present invention. FIG. 1 shows a basic embodiment of the present invention wherein the feed comprising the gaseous mixture is supplied to the lower portion of vessel 1 containing a selectively adsorbing material and magnetizable component 3. A solenoid or magnetic means 5 is arranged to supply a substantially uniform magnetic field on the solid particles charged in vessel 1. The gaseous feed mixture is supplied to the adsorber vessel via line 7. The feedstream from line 7 is fed directly to grid 9 at a superficial fluid velocity sufficient to levitate or fluidize the bed particles. The bed particles leave vessel 1 in a descending manner via standpipe 13. The solids in the standpipe can be controlled by valve means in the standpipe (not shown). These bed particles are then transferred to desorber 21 via line 17. A lift gas from line 15 assists the transfer of the solids in line 17, whereupon the particles empty into desorber vessel 21 via inlet 19. The particles in desorber 21, in a fluidized state, move in a descending manner against the up-flowing gas stream (preferably hot dry gas) provided via line 23. The hot dry gas is fed directly under grid 25. The spent bed particles 3a are stabilized by a solenoid or magnet means 5a. The desorbed or regenerated bed particles flow out of vessel 21 countercurrently and preferably in a plug flow manner into standpipe 29. The regenerated bed particles are then transferred to the adsorber vessel 1 via the standpipe 29 and transfer pipe 31. Transfer of the bed particles may be facilitated by a lift gas via line 15a. The bed particles are returned to vessel 1 via inlet 33. The nature of the selective adsorbent utilized in the process will permit the gases devoid of polar molecules to leave vessel 1 via line 11 while the polar molecules are adsorbed by the bed particles. The adsorbed polar molecules on the other hand are desorbed in desorber 21 and are emitted from the desorber via line 27 along with the hot purge gas. The regenerated particles may be cooled by heat exchanger means (not shown) during passage through line 31 prior to being returned to the top of the adsorber at inlet 33.

Figure 2:
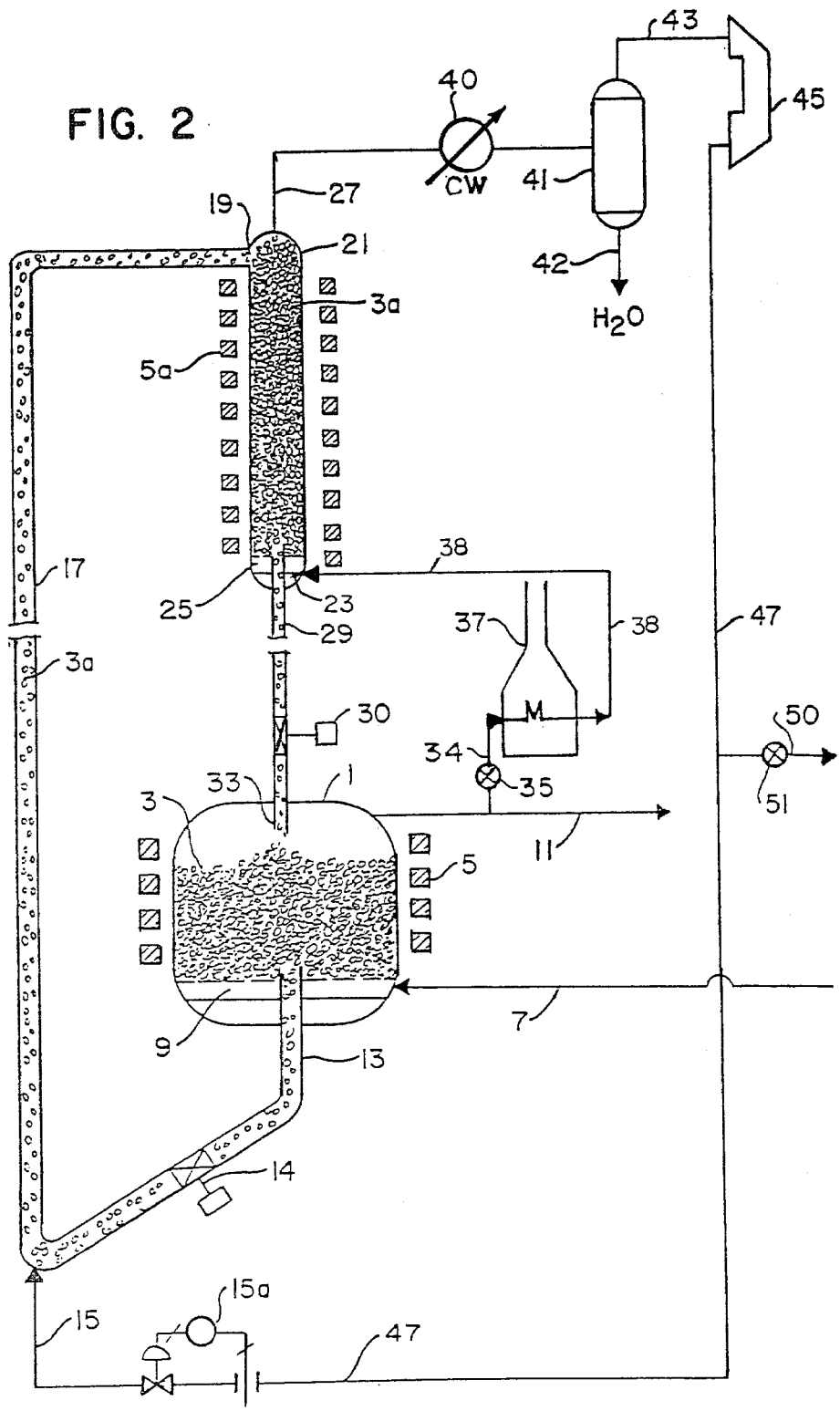
FIG. 2 represents a vertical front cross-sectional view of the magnetically stabilized adsorber and desorber (regenerator) wherein the desorber is positioned above the adsorber.

Referring to FIG. 2, there is shown a separation unit of the present invention which is a study design of a natural gas drying unit preceding liquifaction for LNG. In FIG. 2 there is shown a vertically disposed vessel 1 containing therein a fluidized or expanded or levitated bed 3 of descending sorbent particles which include magnetizable particles. The descending sorbent and magnetizable particles are preferably composites of Type 4A zeolite molecular sieve which has been composited with a 400 Series stainless steel. Surrounding vessel 1 is an arrangement of electrical coils 5 for imposing a magnetic field upon the fluidized bed. A stream of moist gas that is to be dried in the vessel is introduced below the bed through line 7 at a rate sufficient to sustain the bed in a fluidized condition, and dry gas is removed from the vessel above the dense phase of the bed via line 11. The particles that are to be regenerated are removed from the bed via solids outlet 13 controlled by slide valve 14 or its equivalent. The removed solids are carried upward through transfer line 17 to regeneration vessel 21. The solid particles 3a in vessel 21 are levitated in the bed by a suitable rate of flow of regenerating gas introduced through inlet 23. An arrangement of electrical coils 5a surrounds vessel 21 so that a uniform magnetic field can be imposed upon the fluid bed of particles 3a.

Moisture-laden spent regeneration gas leaves the upper portion of vessel 21 via line 27, is cooled in heat exchanger 40 and passes to separator 41. Separated water leaves through line 42, and the dewatered gas passes through line 43 to compressor 45. Regenerated solids are transferred by gravity through line 29, the rate of solids flow being controlled by slide valve 30 or its equivalent.

Although any suitable dry gas could be used for regenerating the solids in vessel 21, it is most advantageous to employ a portion of the dry gas in line 11, leading it into line 34 through valve 35 and heating it in furnace 37. The heated gas is transferred to inlet 23 through line 38.

Most of the dewatered regeneration gas entering compressor 45 is used to convey descending solids from vessel 1 to vessel 21 via transfer line 17, being introduced into that line via valve 15a. Since there would be a net build-up of gas in the circulating system comprising lines 17 and 47, by virtue of the gas added to line 38, an equivalent amount of gas is removed through line 50, controlled by valve 51.

In a representative example using the apparatus of FIG. 2, the temperature and pressure in vessel 1 are 70° F. (21.1° C.) and 625 psig, respectively, and in regeneration vessel 21 they are 600° F. (315.5° C.) and 595 psig, respectively. The particles have a density of 1.6 g/cm$^3$ and an average particle size of 300 microns. To dry 506,000 standard cubic feet per stream day of natural gas containing 1,020 pounds of water per hour to a dew point of $-90°$ F. ($-67.8°$ C.), the bed height is 6 feet, the bed diameter is 12 feet, and the superficial gas velocity is 0.7 feet/sec. in the vessel 1; and a bed height of 15 feet, a bed diameter of 3 feet and a superficial gas velocity of 0.9 feet/sec are used in the regeneration vessel 21. The solids circulation rate through the system is 1,000 pounds per hour. The applied magnetic field is such as to provide a void fraction in both the adsorption and desorption vessels of about 0.35 to about 0.7 or greater. The sorbent particles are a composite of 75 wt. % of the 4A molecular sieve component and 25 wt. % of the ferromagnetic component, the latter being 400 Series stainless steel which is 95 volume percent to 5 volume percent, respectively.

While a single adsorption and desorption vessel is shown in the Drawings, it will be appreciated that multiple vessels may be employed if desired. However, the use of the small particles in the process of the present invention enables one to use fewer or smaller vessels.

What is claimed is:

1. In a process for the selective separation of contaminants from a mixture in a feedstream containing the same within an external force field, said process comprises the steps of:
  (a) adsorbing a portion of said contaminants from said feedstream by contacting said feedstream with a bed comprising adsorbent particles capable of adsorbing said contaminants from said feedstream; and
  (b) desorbing at least a portion of said contaminant from said adsorbent particles in step (a) to regenerate at least a portion of said adsorbent particles;
  the improvement which comprises:
    (1) providing a magnetizable component with said adsorbent particles and applying a magnetic field to said magnetizable component and adsorbent particles along the direction of said external force field and at a strength sufficient to prevent and/or suppress gross solids back-mixing and fluid by-passing;
    (2) expanding or levitating said adsorbent particles and magnetizable component by countercurrently contacting said adsorbent particles and magnetizable component with said feedstream; and
    (3) carrying out said adsorption and desorption steps at substantially the same pressure.

2. The process of claim 1 wherein said applied magnetic field is substantially uniform and said adsorption and desorption steps are carried out in separate vessels.

3. The process of claim 1 or 2 wherein said adsorbent particles and magnetizable component flow in a descending, substantially plug flow manner.

4. The process of claim 1 or 2 wherein the temperature in the adsorption step ranges from about −200° C. to about 350° C. and the pressure in the adsorption and desorption step ranges from about 0.1 to about 2000 psig.

5. The process of claim 1 or 2 wherein said adsorbent particles and magnetizable component have an average mean particle diameter ranging from 50 to about 1500 microns.

6. The process of claim 1 or 2 wherein said adsorbent particles and magnetizable component are composited.

7. The process of claim 1 or 2 wherein said adsorbent particles and magnetizable component are admixed.

8. The process of claim 1 or 2 wherein said adsorbent particles include zeolite molecular sieve particles.

9. The process of claim 1 or 2 wherein said adsorbent particles include activated carbon, treated activated carbon or molecular-sieving carbon particles.

10. The process of claim 1 or 2 wherein said adsorbent particles are selected from non-stoichiometric carbon-sulfur compounds and layered clays.

11. The process of claims 1 or 2 wherein said adsorbent particles are comprised of alumina.

12. The process of claim 1 or 2 wherein the desorption step is carried out by heating the adsorbent particles.

13. The process of claims 1 or 2 wherein a purge stream is utilized during said desorption step and wherein the desorption step is carried out by heating the adsorbent particles.

14. The process of claim 1 or 2 wherein the contaminant loaded adsorbent particles and magnetizable component leave the adsorption zone virtually at equilibrium with the incoming feedstream.

15. The process of claims 1 or 2 wherein said feed stream comprises natural gas and water vapor and the water vapor is preferentially adsorbed during the adsorption step, and wherein the adsorbent particles are comprised of alumina.

16. The process of claims 1 or 2 wherein said feed stream comprises a mixture of methane and ethane and the ethane is preferentially adsorbed during the adsorption step, and wherein said adsorbent particles include activated carbon, treated activated carbon or molecular-sieving carbon particles.

* * * * *